US008672678B2

(12) United States Patent
Gramann et al.

(10) Patent No.: US 8,672,678 B2
(45) Date of Patent: Mar. 18, 2014

(54) POWDER JET DEVICE FOR APPLYING DENTAL MATERIAL

(75) Inventors: Jens Gramann, Munich (DE); Ruediger Hampe, Landsberg (DE); Thomas Klettke, Diessen (DE); Ingo R. Haeberlein, Weilheim (DE); Christoph Schulte, Windach (DE); Andreas R. Maurer, Langenneufnach (DE); Martin Goetzinger, Eching a.Ammersee (DE); Sebastian Guggenmos, Peissenberg (DE)

(73) Assignee: 3M Innovative Properties Company, St. Paul, MN (US)

( * ) Notice: Subject to any disclaimer, the term of this patent is extended or adjusted under 35 U.S.C. 154(b) by 84 days.

(21) Appl. No.: 12/994,917

(22) PCT Filed: May 28, 2009

(86) PCT No.: PCT/US2009/045374
§ 371 (c)(1),
(2), (4) Date: Nov. 29, 2010

(87) PCT Pub. No.: WO2009/148907
PCT Pub. Date: Dec. 10, 2009

(65) Prior Publication Data
US 2011/0076639 A1    Mar. 31, 2011

(30) Foreign Application Priority Data
Jun. 6, 2008 (GB) .................................. 0810384.8

(51) Int. Cl.
*A61C 3/02* (2006.01)
(52) U.S. Cl.
USPC .......................................................... 433/88
(58) Field of Classification Search
USPC ............ 433/88, 89, 90, 87; 60/740, 741, 742; 239/76, 116; 128/200.14, 200.19; 451/36–40, 28
See application file for complete search history.

(56) References Cited

U.S. PATENT DOCUMENTS 1,786,946 A * 12/1930 Hofmann ......................... 60/741
2,709,852 A *  6/1955 Maurer et al. .................. 433/29
(Continued)

FOREIGN PATENT DOCUMENTS

CA          2255454         6/1993
CA          2286876         4/2000
(Continued)

OTHER PUBLICATIONS

International Search Report PCT/US2009/045374, Apr. 9, 2009, 2 pgs.
(Continued)

*Primary Examiner* — Cris L Rodriguez
*Assistant Examiner* — Mirayda A Aponte
(74) *Attorney, Agent, or Firm* — Nicole J. Einerson

(57) ABSTRACT

A nozzle head (5) for a powder jet device (1), for use in applying dental material, comprises a first fluid flow path (8) for delivering a powder/fluid mixture to a first discharge nozzle (8A). A second fluid flow path (6) is provided for delivering a liquid to a second discharge nozzle (6A) located adjacent the first discharge nozzle (8A), so that the materials discharged by the first and second discharge nozzles combine at a desired location to form a dental composition. A nozzle-clearing member (10) is located inside the nozzle head and is movable to remove powder material from the first discharge nozzle when the flow of powder/fluid mixture to the nozzle ceases.

13 Claims, 3 Drawing Sheets

(56) References Cited

U.S. PATENT DOCUMENTS

| | | | |
|---|---|---|---|
| 2,842,160 A * | 7/1958 | Rekettye | 137/565.11 |
| 2,991,945 A * | 7/1961 | Rosenkranz | 239/459 |
| 3,001,723 A * | 9/1961 | Bounds | 239/448 |
| 3,448,929 A * | 6/1969 | Strahman et al. | 239/288.5 |
| 3,586,044 A | 6/1971 | Petersen | |
| 3,919,775 A | 11/1975 | Malmin | |
| 3,972,123 A | 8/1976 | Black | |
| 4,133,483 A | 1/1979 | Henderson | |
| 4,223,838 A | 9/1980 | Maria-Vittorio-Torrisi | |
| 4,384,674 A * | 5/1983 | Somerville | 239/118 |
| 4,534,512 A * | 8/1985 | Chow et al. | 239/394 |
| 4,676,749 A * | 6/1987 | Mabille | 433/88 |
| 4,950,160 A * | 8/1990 | Karst | 433/88 |
| 5,007,837 A | 4/1991 | Werly | |
| 5,094,615 A | 3/1992 | Bailey | |
| 5,119,991 A | 6/1992 | Divers | |
| 5,199,229 A | 4/1993 | Herold | |
| 5,716,003 A | 2/1998 | Streetman | |
| 6,120,755 A | 9/2000 | Jacobs | |
| 6,312,261 B1 | 11/2001 | Mays | |
| 6,315,565 B1 | 11/2001 | Slotke | |
| 6,390,816 B2 * | 5/2002 | Ito et al. | 433/88 |
| 6,464,570 B1 * | 10/2002 | Shaw et al. | 451/102 |
| 6,676,409 B2 | 1/2004 | Grant | |
| 6,755,650 B2 | 6/2004 | Decosterd | |
| 6,884,070 B2 | 4/2005 | Cevey | |
| 6,910,887 B2 | 6/2005 | Van Den Houdt | |
| 7,011,521 B2 * | 3/2006 | Sierro et al. | 433/88 |
| 7,040,960 B2 | 5/2006 | Hench | |
| 7,083,411 B2 | 8/2006 | Flemmig | |
| 7,198,485 B2 * | 4/2007 | Hamman | 433/88 |
| 2001/0031441 A1 | 10/2001 | Ito | |
| 2002/0004188 A1 | 1/2002 | Beerstecher | |
| 2002/0137004 A1 | 9/2002 | Sierro | |
| 2003/0129560 A1 | 7/2003 | Atkin et al. | |
| 2004/0202980 A1 | 10/2004 | Policicchio | |
| 2004/0265773 A1 | 12/2004 | Mariaulle | |
| 2005/0202364 A1 | 9/2005 | Fornasari | |
| 2005/0233280 A1 | 10/2005 | Hamman | |
| 2007/0042316 A1 | 2/2007 | Pichat | |
| 2007/0080240 A1 | 4/2007 | Schuetz | |
| 2010/0261143 A1 | 10/2010 | Schulte et al. | |
| 2011/0076639 A1 * | 3/2011 | Gramann et al. | 433/88 |

FOREIGN PATENT DOCUMENTS

| | | |
|---|---|---|
| CA | 2361623 | 8/2000 |
| CA | 2343867 | 5/2002 |
| CA | 2457169 | 8/2004 |
| DE | 9213308 | 1/1993 |
| DE | 4332226 | 3/1995 |
| DE | 4404954 | 8/1995 |
| DE | 29508873 | 10/1996 |
| DE | 19643931 | 4/1998 |
| DE | 29810580 | 10/1999 |
| DE | 19804065 | 12/1999 |
| DE | 19916153 | 10/2000 |
| DE | 10111856 | 10/2002 |
| DE | 10345107 | 5/2005 |
| EP | 0726737 | 3/2000 |
| EP | 1145689 | 10/2001 |
| EP | 1223884 | 8/2006 |
| GB | 2026359 | 2/1980 |
| GB | 2289427 | 11/1995 |
| JP | 09-276292 | 10/1997 |
| JP | 10-323352 | 12/1998 |
| JP | 11-104148 | 4/1999 |
| JP | 11-192244 | 7/1999 |
| JP | 11-244303 | 9/1999 |
| JP | 2001-354536 | 12/2001 |
| JP | 2002-209911 | 7/2002 |
| JP | 2002-238923 | 8/2002 |
| JP | 2005-296822 | 10/2005 |
| JP | 2006-198355 | 8/2006 |
| WO | WO 96/02207 | 2/1996 |
| WO | WO 98/12981 | 4/1998 |
| WO | WO 02/074180 | 9/2002 |
| WO | WO 2004/071326 | 8/2004 |

OTHER PUBLICATIONS

Patent Search Report, Application No. 200980120697.3 Jul. 24, 2012, 2 pgs.

* cited by examiner

POWDER JET DEVICE FOR APPLYING DENTAL MATERIAL

CROSS REFERENCE TO RELATED APPLICATIONS

This is a national stage filing under 35 U.S.C. 371 of PCT/US2009/045374, filed May 28, 2009, which claims priority to GB Application No. 0810384.8, filed Jun. 6, 2008, the disclosure of which is incorporated by reference in its entirety herein.

The present invention relates to a powder jet device for use in applying dental material to a desired location, for example the tooth structure of a patient.

Various devices are known for applying dental materials. They include the powder jet devices that are currently used for applying a stream of abrasive particles and water to the tooth structure of a patient for cleaning the tooth surfaces.

Generally, a powder jet device comprises a nozzle through which a stream of pressurized fluid containing powder material is delivered. When the pressurized fluid is a gas, a stream of pressurized liquid may also be delivered by the device at the same time as the powder/gas stream, for example through a separate nozzle. When a device of that type is used for cleaning tooth surfaces, the powder material comprises dental abrasive particles, the gas is normally air and the liquid is normally water.

Examples of powder jet devices for use in the field of dentistry are described in U.S. Pat. No. 3,972,123 (Black); U.S. Pat. No. 4,676,749 (Mabille); GB-A-2 026 359 (Gallant); JP-A-11104148 (Micron KK); US-A-2003/0129560 (Atkin et al); and WO 03/011164 (Medivance Instruments Limited)

Some powder materials, when delivered through a nozzle of a powder jet device, may tend to block the nozzle. That may be the case, especially (but not exclusively), if the powder comes into contact with a liquid (e.g. a stream of water as described above, or even just moisture) as it emerges from the nozzle because the powder may become damp and flow less freely than when it is dry. In a more extreme case, the powder may be intended to form a hardenable paste or gel when mixed with the fluid and can, therefore be expected to block the nozzle unless removed. With that in mind, some powder jet devices for use in the field of dentistry are provided with disposable nozzles (see, for example, the above-mentioned US-A-2003/0129560). It has also been proposed, in the above-mentioned JP-A-11104148, WO 03/011164 and GB-A-2 026 359, to pass a stream of pressurized gas through the nozzle of a powder jet device specifically for the purpose of cleaning it.

The present invention is directed to the problem of reducing the risk of a discharge nozzle of a powder-jet device becoming blocked during use, so that the nozzle can be re-used without substantially increasing the complexity, or diminishing the robustness, of the nozzle construction.

The present invention provides a nozzle head for a powder jet device for use in applying dental material, the nozzle head comprising:
a first fluid flow path for delivery, to a first discharge nozzle, of a powder material carried by a fluid; and
a nozzle-clearing member located inside the nozzle head and movable to remove powder material from the first discharge nozzle when the flow of powder-carrying fluid to the nozzle ceases.

The nozzle-clearing member may, for example, comprise a nozzle-clearing portion that is movable into the first discharge nozzle to remove accumulated powder material; alternatively, the nozzle-clearing portion may be movable within the first discharge nozzle. In an embodiment of the invention, the nozzle-clearing portion has the form of a pin with a diameter comparable to that of the nozzle and is movable into the first discharge nozzle to remove accumulated powder material.

The nozzle clearing member may be movable in response to fluid pressure in the first fluid flow path and, to that end, may comprise a plunger exposed to fluid flow in the first fluid flow path. Alternatively, the nozzle clearing member may be movable in response to actuation of control means regulating the supply of powder-carrying fluid to the nozzle.

When a nozzle head in accordance with the invention is used in a powder jet device of the general type described above, the first fluid flow path is supplied with fluid (for example, air) carrying the powder material. When the flow of the powder/fluid mixture ceases, the nozzle-clearing member moves to remove powder material from the first discharge nozzle thereby reducing the risk that the nozzle will become blocked, and allowing the nozzle head to be re-used.

A nozzle head in accordance with the invention may further comprise a second fluid flow path to a second discharge nozzle located adjacent the first discharge nozzle. When such a nozzle head is used in a powder jet device of the general type described above, the second fluid flow path may be connected to a source of liquid, for example water.

By way of example, a powder jet device having a nozzle head in accordance with the invention will now be described with reference to the accompanying drawings, in which.

Figure 1:
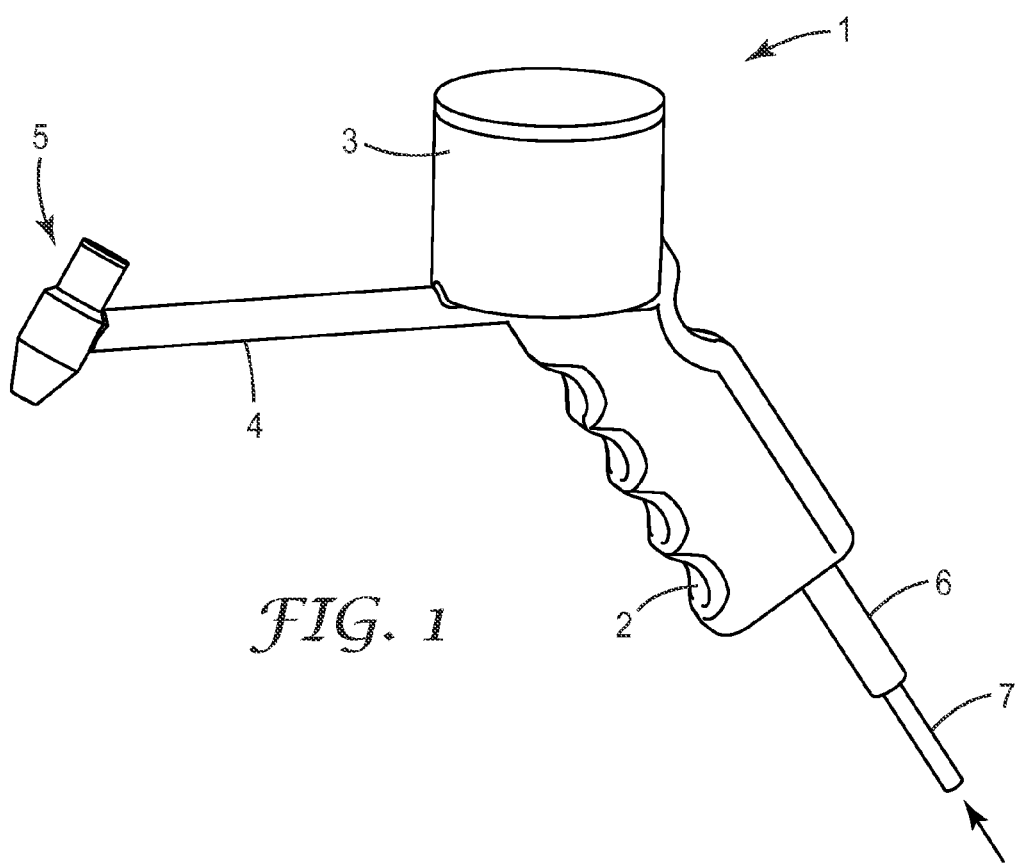
FIG. 1 is a side view of the device.

The powder jet device 1 shown in the drawings is of a type for use in the dental field for applying a powder/gas mixture and a liquid to the tooth structure of a patient.

Figure 2:
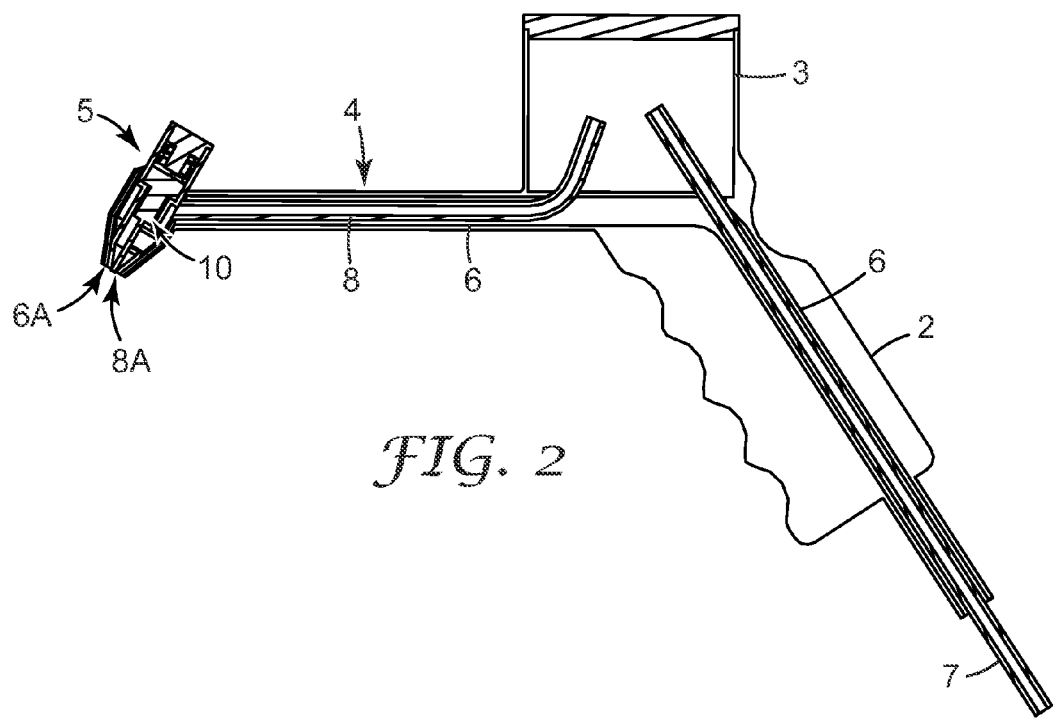
FIG. 2 shows a longitudinal cross-section through the device.

The device 1 is in the form of a hand-piece comprising a handgrip 2, a powder reservoir 3 and a delivery arm 4 terminating in a nozzle head 5. As shown in FIG. 2, a liquid supply line 6 passes through the handgrip 2 and the delivery arm 4 of the handpiece to the nozzle head 5; a gas supply line 7 passes through the handgrip 2 into the powder reservoir 3; and a powder/gas supply line 8 passes through the delivery arm 4 from within the powder reservoir to the nozzle head 5. The gas supply line 7 is located within the liquid supply line 6, at least for its passage through the handgrip 2, and the powder/gas supply line 8 is likewise located within the liquid supply line 6 for its passage along the delivery arm 4.

The device 1 can be used to apply various dental materials but, for the purposes of the present description, it is assumed that the device will be used to apply a hardenable dental composition to the tooth structure of a patient. The dental composition may, for example, harden into a highly-viscous paste or gel and may, for example, be a dental retraction composition used to retract soft dental tissue away from hard dental tissue and thereby open the sulcus temporarily, for example to enable a dental impression to be taken. It is further assumed, for the purposes of the present description, that the dental composition is formed by combining a suitable powder material with a liquid, for example water or a salt solution. Examples of powder materials that the device can be used to apply are those described in our co-pending European patent application No. 07122768.0, filed 10 Dec. 2007 and entitled "Dental Retraction Composition, Production thereof and Use of a Powder Jet Device for Dental Refraction".

In use of the device 1, the powder material required for the dental retraction composition is contained within the powder reservoir 3, and the supply line 6 of the device is connected to a pressurized source of the liquid. The gas supply line 7 is connected to a pressurized source of a gas suitable for dental use and for transporting the powder material. The gas may, for example, be air. The sources of pressurized liquid and gas, and the controls for regulating their supply, are not shown and may be at any suitable remote location. Alternatively, the supply may be regulated by a trigger or a similar device in the handgrip 2.

The pressurized gas delivered by the supply line 7 into the powder reservoir 3 produces a powder/gas mixture in the reservoir, which passes along the supply line 8 in the delivery arm 4 towards the nozzle head 5 from where it is discharged through a respective nozzle 8A. While that is happening, pressurized liquid is supplied along the supply line 6 towards the nozzle head 5 from where it is discharged through a respective nozzle 6A and is directed, along with the air/powder mixture, to the tooth structure of the patient where the powder and the liquid combine to form the hardenable dental composition.

Figure 3:
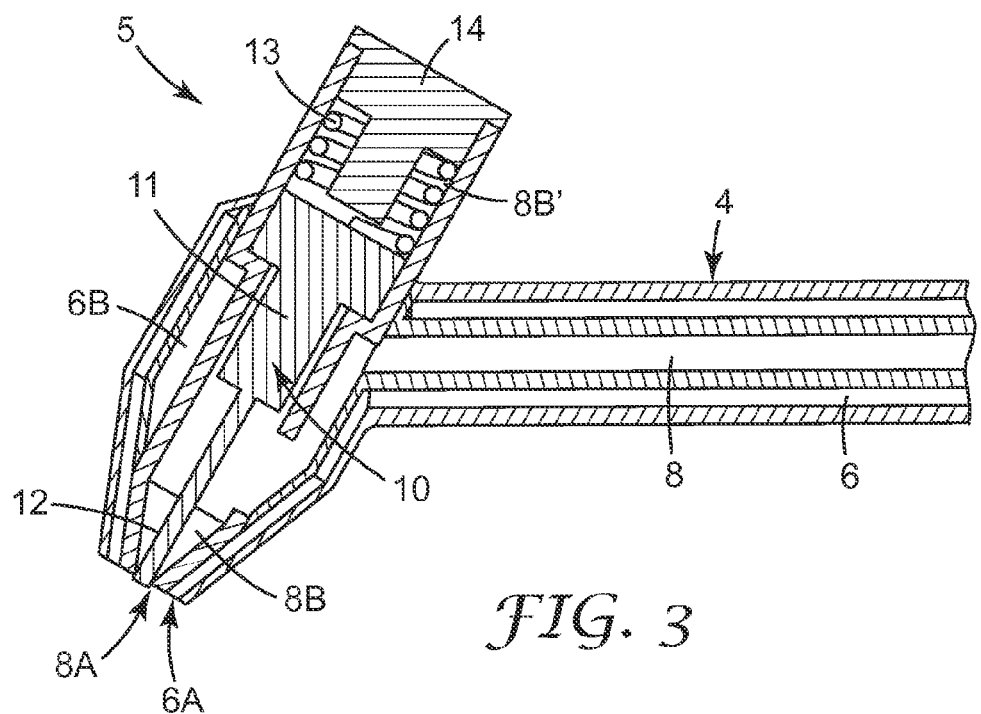
FIG. 3 is an enlarged view of part of the device of FIG. 2, showing the nozzle head of the device in a closed condition.
Figure 4:
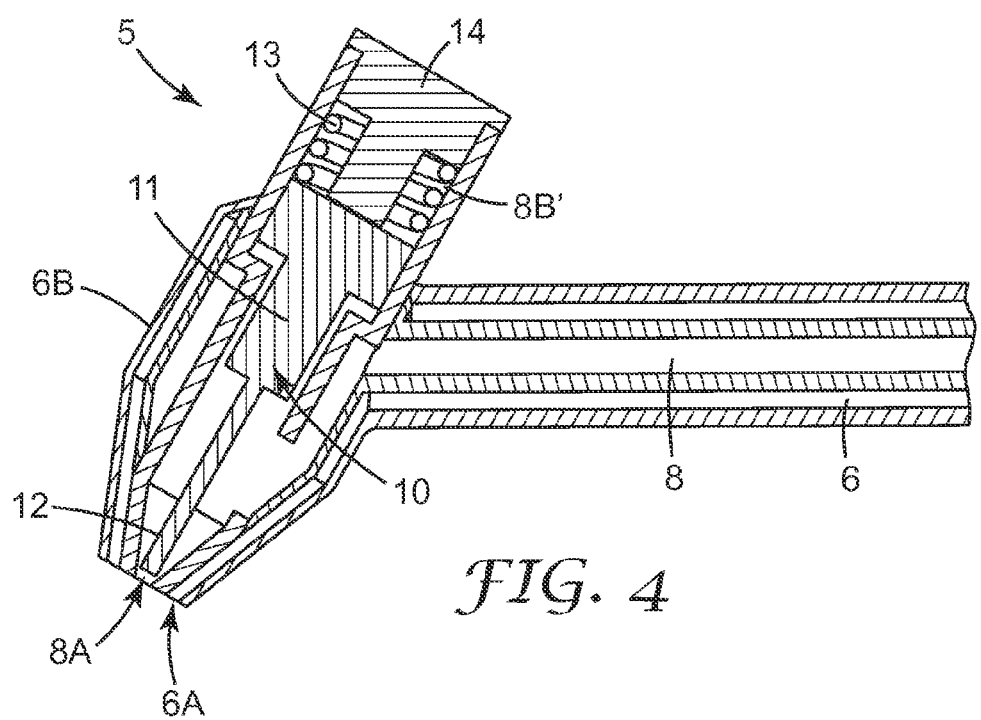
FIG. 4 is similar to FIG. 3 but shows the nozzle head in an open condition.

The structure of the nozzle head 5 is shown in greater detail in FIGS. 3 and 4. The nozzle head comprises an inner chamber 8B surrounded by an outer chamber 6B. The inner chamber 8B is connected to receive powder/gas mixture from the supply line 8 in the delivery arm 4 of the powder jet device 1, and the outer chamber 6B is connected to receive liquid from the supply line 6. The nozzle 6A, which is the outlet from the chamber 6B, surrounds the nozzle 8A, which is the outlet from the chamber 8B with the result that the powder/gas mixture is delivered by the nozzle head 5 in a stream surrounded by a curtain of liquid. The nozzle head 5 is positioned to direct the emerging powder/gas and liquid streams at an angle to the longitudinal axis of the delivery arm 4 to facilitate the accurate delivery of the materials to the target site in the patient's mouth.

The concentric arrangement of the nozzles 6A, 8A is advantageous in that the curtain of liquid surrounding the powder/gas mixture reduces the risk of introducing dust into the environment in which the powder jet device 1 is used. There is, however, a risk that powder will accumulate on, and block, the nozzle 8A, particularly if the powder is one that is intended to harden rapidly to a paste or gel when mixed with liquid. To reduce the risk of the nozzle 8A becoming blocked, the nozzle head 5 includes a nozzle-clearing member 10 that functions to remove material from within the nozzle 8A whenever the flow of material through the inner chamber 8B ceases.

The nozzle-clearing member 10 is located within the inner chamber 8B of the nozzle head 5, and a rearward chamber extension 8B'. The nozzle-clearing member 10 comprises a plunger 11 from the front face of which extends an elongate nozzle-clearing portion in the form of a pin 12 having a diameter comparable to that of the nozzle 8A. A spring 13, located in the chamber extension 8B', acts on the rear face of the plunger 11 to urge the plunger towards a position (shown in FIG. 3) in which the pin 12 extends into the nozzle 8A and effectively closes the latter. The spring is supported on an adjustment screw 14 in the end of the chamber extension 8B', enabling the closed position of the plunger 11 to be adjusted to ensure the removal of powder material from within the nozzle 8A by the pin 12 as it moves into the nozzle.

The front face of the plunger 11 is exposed to the pressure generated in the inner chamber 8B of the nozzle head 5 by the flow of powder/gas mixture through the chamber. During normal use of the powder jet device 1, that pressure is sufficient to move the plunger 11 backwards in the chamber 8B against the force of the spring 13 thereby moving the pin 12 out of the nozzle 8A and into the open position shown in FIG. 4. When the flow of the powder/gas mixture ceases, the pressure on the front face of the plunger 11 drops and the plunger returns to the closed position shown in FIG. 3 under the force of the spring 13. The pin 12 is moved back into the nozzle 8A, in the course of which it removes powder material that may have collected in the nozzle, before the material can harden and block the nozzle.

The particular construction of the powder jet device 1 shown in the drawings is an exemplary embodiment only of the invention. Any suitable powder jet device could be modified by the inclusion of a nozzle-clearing member 10 as described above. In some powder jet devices, for example, the powder reservoir 3 is a separate component and does not form part of the hand-piece 1. The arrangement of the various supply lines 6, 7, 8 can also be modified, for example so that they are positioned side-by-side rather than one inside the other. Likewise, the concentric arrangement of the discharge nozzles 6A, 8A, although advantageous, is not essential: an alternative arrangement, in which the discharge nozzles 6A, 8A are positioned side-by-side is, for example, also possible.

It will be understood that the above-described use of the powder jet device 1 to apply a dental retraction composition is one example only of the uses of powder jet devices in the dental field. A powder jet device having a nozzle head in accordance with the invention could be use to apply a variety of dental compositions, some of which may not be intended to harden or to remain in position after application, some of which may need to be cured after application, and others of which may comprise components that react chemically with one another after application. A powder jet device having a nozzle head in accordance with the invention may, for example, be used to apply a mixture of abrasive particles and water for cleaning the surfaces of a patient's teeth.

Although a powder jet device typically uses a stream of gas to transport the powder material, that is not essential and a stream of liquid could be used instead, when appropriate. When a stream of gas is used, any appropriate gas can be selected that is not detrimental to the patient, and does not react in an unwanted manner with the powder material or any other materials with which it may come into contact. Typically, however, air is preferred.

In some cases, there may be no need to discharge a liquid from the nozzle head of the powder jet device at the same time as the powder/gas mixture. In that case, the liquid supply to the nozzle head can be omitted. Even when a liquid is to be applied with the gas/powder mixture, it need not be applied from the nozzle head of the powder jet device but could be applied from a separate source. It is also not essential for the liquid to be applied at exactly the same time as the powder/gas mixture: in some cases, for example, it may be more appropriate for the application of the liquid not to commence until the flow of the powder/gas mixture is already established. When a liquid is applied with the powder/gas mixture, any appropriate liquid can be selected that is not detrimental to the patient, and functions in the required manner when in combination with the powder material. The liquid may, for example, be required to dissolve the powder material applied by the powder jet device, or to combine with it to form a dispersion, an emulsion or a gel, or to cause the powder to swell. Examples of other liquids that may be selected are alcohols and ketones. Typically, however, water is preferred.

Alternative arrangements for moving the nozzle-clearing member 10 are also possible. The nozzle-clearing member could, for example, be arranged to move in response to actuation of a trigger in the handgrip 2 that controls the supply of gas to the powder reservoir 3. In such a case, the actual movement of the nozzle-clearing member could be effected by, for example, a suitable motor or a solenoid actuator. The actual form of the nozzle-clearing portion 12 can also be modified, for example from a component that moves into and out of the nozzle 8A to one that rotates within the nozzle and thereby removes powder material from the nozzle.

The invention claimed is:

1. A nozzle head for a powder jet device for use in applying dental material, the nozzle head comprising:
   a first fluid flow path for delivery, to a first discharge nozzle, of a powder material carried by a fluid; and
   a nozzle-clearing member located inside the nozzle head and movable into or within the first discharge nozzle to remove powder material from the first discharge nozzle when the flow of powder-carrying fluid to the nozzle ceases, wherein the nozzle-clearing member is movable between a closed position in which the clearing member extends into the first discharge nozzle, and an open position in which the clearing member is removed from the first discharge nozzle.

2. A nozzle head as claimed in claim 1, further comprising a second fluid flow path to a second discharge nozzle located adjacent the first discharge nozzle.

3. A nozzle head as claimed in claim 2, in which the second discharge nozzle surrounds the first discharge nozzle.

4. A powder jet device comprising a nozzle head as claimed in claim 1, in which the first fluid flow path is connected to a source of fluid carrying the powder material.

5. A device as claimed in claim 4, in which the fluid is a gas.

6. A powder jet device comprising a nozzle head as claimed in claim 2, in which the second fluid flow path is connected to a source of liquid.

7. A device as claimed in claim 6, in which the liquid and the powder material are components of a dental composition.

8. A device as claimed in claim 4, in the form of a hand-piece on which the nozzle head is mounted.

9. A device as claimed in claim 8, in which the hand-piece comprises a reservoir for containing the powder material.

10. A method of using a device as claimed in claim 7 to form a dental composition at a desired location, comprising the step of positioning the nozzle head so that the materials discharged by the first and second discharge nozzles combine at the desired location.

11. A device as claimed in claim 1, wherein the first discharge nozzle is an outlet of the first fluid flow path.

12. A nozzle head as claimed in claim 1, in which the nozzle-clearing member comprises a plunger that is resiliently-biased towards a position corresponding to the closed position of the nozzle-clearing member, the plunger being movable by fluid pressure in the first flow path into a position corresponding to the open position of the nozzle-clearing member.

13. A nozzle head as claimed in claim 12, in which the nozzle-clearing member comprises an elongate nozzle-clearing portion that extends from the plunger to move into the first discharge nozzle when the nozzle-clearing member moves into the closed position.

\* \* \* \* \*

UNITED STATES PATENT AND TRADEMARK OFFICE
CERTIFICATE OF CORRECTION

PATENT NO. : 8,672,678 B2  
APPLICATION NO. : 12/994917  
DATED : March 18, 2014  
INVENTOR(S) : Gramann et al.

Page 1 of 1

It is certified that error appears in the above-identified patent and that said Letters Patent is hereby corrected as shown below:

In the Specification

Column 1  
Line 33, Delete "Limited)" and insert -- Limited). --, therefor.

Column 3  
Line 2, Delete "Refraction" and insert -- Retraction --, therefor.

Signed and Sealed this  
Seventeenth Day of June, 2014

Michelle K. Lee  
*Deputy Director of the United States Patent and Trademark Office*